(12) United States Patent
Jin et al.

(10) Patent No.: US 12,348,872 B2
(45) Date of Patent: Jul. 1, 2025

(54) AUTONOMOUS PHENOTYPE IMAGING SYSTEM

(71) Applicant: Purdue Research Foundation, West Lafayette, IN (US)

(72) Inventors: Jian Jin, West Lafayette, IN (US); Xuan Li, Lafayette, IN (US); Ziling Chen, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 71 days.

(21) Appl. No.: 18/387,986

(22) Filed: Nov. 8, 2023

(65) Prior Publication Data
US 2024/0155240 A1    May 9, 2024

Related U.S. Application Data

(60) Provisional application No. 63/423,771, filed on Nov. 8, 2022, provisional application No. 63/423,773, filed on Nov. 8, 2022.

(51) Int. Cl.
*H04N 23/13* (2023.01)
*A01G 7/00* (2006.01)
(Continued)

(52) U.S. Cl.
CPC ............. *H04N 23/695* (2023.01); *A01G 7/00* (2013.01); *G06V 10/143* (2022.01);
(Continued)

(58) Field of Classification Search
None
See application file for complete search history.

(56) References Cited

U.S. PATENT DOCUMENTS

| 2018/0035606 | A1* | 2/2018 | Burdoucci | A01D 34/008 |
| 2019/0107440 | A1* | 4/2019 | Pluvinage | G01J 3/0297 |
| 2022/0117218 | A1* | 4/2022 | Sibley | B23K 26/0884 |

FOREIGN PATENT DOCUMENTS

CN    207589606    *    7/2018

OTHER PUBLICATIONS

Zhang et al., (2019). Optimized angles of the swing hyperspectral imaging system for single corn plant. Computers and Electronics in Agriculture, 156, 349-359.

(Continued)

*Primary Examiner* — Eileen M Adams
(74) *Attorney, Agent, or Firm* — Piroozi-IP, LLC

(57) ABSTRACT

An autonomous system for providing consistent images of leaves of plants is disclosed which includes a mobility unit configured to move from an originating position to a position about a plant in a field, one or more vacuum units coupled to the mobility unit configured to be positioned above one or more leaves of the plant, the one or more vacuum units each having one or more fans coupled to an air inlet having a grate, and configured to elevate the one or more leaves of the plant onto the grate, one or more imaging systems each having one or more cameras configured to obtain images from the one or more leaves of the plant, and a controller configured to control position of the mobility unit and activate the one or more imaging system to thereby obtain images from the one or more leaves of the plant.

23 Claims, 14 Drawing Sheets
(10 of 14 Drawing Sheet(s) Filed in Color)

(51) Int. Cl.
| | |
|---|---|
| G06V 10/143 | (2022.01) |
| G06V 10/26 | (2022.01) |
| G06V 20/10 | (2022.01) |
| H04N 13/207 | (2018.01) |
| H04N 13/271 | (2018.01) |
| H04N 23/56 | (2023.01) |
| H04N 23/695 | (2023.01) |
| B64U 10/13 | (2023.01) |
| B64U 101/30 | (2023.01) |

(52) U.S. Cl.
CPC .......... *G06V 10/273* (2022.01); *G06V 20/188* (2022.01); *G06V 20/194* (2022.01); *H04N 13/207* (2018.05); *H04N 13/271* (2018.05); *H04N 23/13* (2023.01); *H04N 23/56* (2023.01); *B64U 10/13* (2023.01); *B64U 2101/30* (2023.01); *B64U 2201/10* (2023.01)

(56) References Cited

OTHER PUBLICATIONS

Zhang et al., (2019). Establishment of Plot-Yield Prediction Models in Soybean Breeding Programs Using UAV-Based Hyperspectral Remote Sensing. Remote Sensing, 11(23).
Zheng et al., (2012). Leaf orientation retrieval from terrestrial laser scanning (TLS) data. IEEE Transactions on Geoscience and Remote Sensing, 50(10), 3970-3979.
Geldhof et al., (2021). A digital sensor to measure real-time leaf movements and detect abiotic stress in plants. Plant Physiology, 187(3), 1131-1148.
Zhang et al., (2012). Robust hyperspectral vision-based classification for multi-season weed mapping. ISPRS Journal of Photogrammetry and Remote Sensing, 69, 65-73.
Li et al., (2022). Robotic crop row tracking around weeds using cereal-specific features. Computers and Electronics in Agriculture, 197, 106941.
Blad et al., (1972). Orientation and distribution of leaves within soybean canopies. Agronomy Journal, 64(1), 26-29.
Biskup et al., (2007). A stereo imaging system for measuring structural parameters of plant canopies. Plant, Cell & Environment, 30(10).
Wang et al., LeafScope: A Portable High-Resolution Multispectral Imager for In Vivo Imaging Soybean Leaf. Sensors, 20(8), 2194.
Jinendra et al., (2010). Near infrared spectroscopy and aquaphotomics: Novel approach for rapid in vivo diagnosis of virus infected soybean. Biochemical and Biophysical Research Communications, 397(4), 685-690.
Bradley et al., (2021). Soybean Yield Loss Estimates Due to Diseases in the United States and Ontario, Canada, from 2015 to 2019. Plant Health Progress, 22(4), 483-495.
Chen et al., (2021). Automated in-field leaf-level hyperspectral imaging of corn plants using a Cartesian robotic platform. Computers and Electronics in Agriculture, 183, 105996.
Cui et al., (2009). Detection of soybean rust using a multispectral image sensor. Sensing and Instrumentation for Food Quality and Safety, 3(1), 49-56.
Da Silva Junior et al., (2018). Soybean varieties discrimination using non-imaging hyperspectral sensor. Infrared Physics and Technology, 89, 338-350.
Fletcher et al., (2016). Random forest and leaf multispectral reflectance data to differentiate three soybean varieties from two pigweeds. Computers and Electronics in Agriculture, 128, 199-206.
Gowen et al., (2007). Hyperspectral imaging—an emerging process analytical tool for food quality and safety control. Trends in Food Science and Technology, 18(12), 590-598.
Gui et al., (2021). Grading method of soybean mosaic disease based on hyperspectral imaging technology. Information Processing in Agriculture, 8(3), 380-385.
Guilherme et al., (2021). Using leaf-based hyperspectral reflectance for genotype classification within a soybean germplasm collection assessed under different levels of water availability. International Journal of Remote Sensing, 42(21), 8165-8184.
Kao et al., (1992). Dirunal leaf movement, chlorophyll fluorescence and carbon assimilation in soybean grown under different nitrogen and water availabilities. Plant, Cell & Environment, 15(6), 703-710.
Kovar et al., (2019). Evaluation of hyperspectral reflectance parameters to assess the leaf water content in soybean. Water (Switzerland), 11(3), 1-12.
Ma et al., (2021a). Modeling of diurnal changing patterns in airborne crop remote sensing images. Remote Sensing, 13(9), 1-19.
Pandey et al., (2017). High Throughput In vivo Analysis of Plant Leaf Chemical Properties Using Hyperspectral Imaging. Frontiers in Plant Science, 8, 1348.
Rehman et al., (2020). Calibration transfer across multiple hyperspectral imaging-based plant phenotyping systems: I—Spectral space adjustment. Computers and Electronics in Agriculture, 176, 105685.
Wang (2021). Automated Leaf-Level Hyperspectral Imaging of Soybean Plants using an UAV with a 6 DOF Robotic Arm.
Wang et al., (2020). LeafSpec: An accurate and portable hyperspectral corn leaf imager. Computers and Electronics in Agriculture, 169, 105209.
Yuan et al., (2017). Retrieving Soybean Leaf Area Index from Unmanned Aerial Vehicle Hyperspectral Remote Sensing: Analysis of RF, ANN, and SVM Regression Models. Remote Sensing, 9(4).
Zhang et al., (2019). Assessing crop damage from dicamba on non-dicamba-tolerant soybean by hyperspectral imaging through machine learning. Pest Management Science, 75(12), 3260-3272.

\* cited by examiner

AUTONOMOUS PHENOTYPE IMAGING SYSTEM

CROSS-REFERENCE TO RELATED APPLICATIONS

The present non-provisional patent application is related to and claims the priority benefit of U.S. Provisional Patent Application Ser. No. 63/423,771, filed Nov. 8, 2022, and also claims the priority benefit of U.S. Provisional Patent Application Ser. No. 63/423,773, filed Nov. 8, 2022, the contents of each of which are hereby incorporated by reference in its entirety into the present disclosure.

STATEMENT REGARDING GOVERNMENT FUNDING

None.

TECHNICAL FIELD

The present disclosure generally relates to plant phenotypic systems, and in particular to a plant phenotyping imaging system with a vacuum-based leaf-handling mechanism.

BACKGROUND

This section introduces aspects that may help facilitate a better understanding of the disclosure. Accordingly, these statements are to be read in this light and are not to be understood as admissions about what is or is not prior art.

A high throughput plant phenotyping system is required for plant researchers and precision agriculture in order improve high yields and also develop new genotype as well as to monitor plant health. Specifically, precision agriculture is now ubiquitously used to optimize crop yield especially in light of decades-long drought conditions in vast areas of the country by using systems with feedback to provide water where needed, improve monitoring of crop health, and minimizing environmental impact by optimizing fertilizers and insecticides to only area where these potentially harmful chemicals are deemed to be necessary. Furthermore, where new plants are being planted, it is necessary to understand and quantify plant growth and structure at a large scale.

Various imaging techniques have been used to image leaves of plants for determination of plant health. One such imaging technique is based on Hyperspectral Imaging system (HIS) which require placement of the leaf in a flat and repeatable manner for any automatic imaging system. However, automatic leaf-handling mechanisms suffer from inconsistently accepting leaves into an imaging chamber; thus, resulting in loss of quality and necessity for repeating the imaging procedures.

Therefore, there is an unmet need for a novel imaging system that can provide consistent phenotyping images of a large number of plants and their associated leaves to be used for high precision agriculture and phenotyping studies such that leaves of plants are processed consistently.

SUMMARY

An autonomous system for providing consistent images of leaves of plants is disclosed. The system includes a mobility unit configured to move from an originating position to a position about a plant in a field. The system further includes one or more vacuum units coupled to the mobility unit configured to be positioned above one or more leaves of the plant. The one or more vacuum units each having one or more fans coupled to an air inlet having a grate, and configured to elevate the one or more leaves of the plant onto the grate. The system also includes one or more imaging systems each having one or more cameras configured to obtain images from the one or more leaves of the plant. The system also includes a controller configured to control position of the mobility unit and activate the one or more imaging system to thereby obtain images from the one or more leaves of the plant.

A method of autonomously providing consistent images of leaves of plants is also disclosed. The method includes moving a mobility unit from an originating position to a position about a plant in a field. The method further includes positioning one or more vacuum units coupled to the mobility unit above one or more leaves of the plant. The one or more vacuum units each having one or more fans coupled to an air inlet having a grate, and configured to elevate the one or more leaves of the plant onto the grate. The method also includes obtaining images from the one or more leaves of the plant by one or more imaging systems each having one or more cameras. Additionally, the method includes controlling position of the mobility unit by a controller and activate the one or more imaging system to thereby obtain images from the one or more leaves of the plant.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 4b is a mask used to remove the background information presented in FIG. 4a.

DETAILED DESCRIPTION

Figure 1:
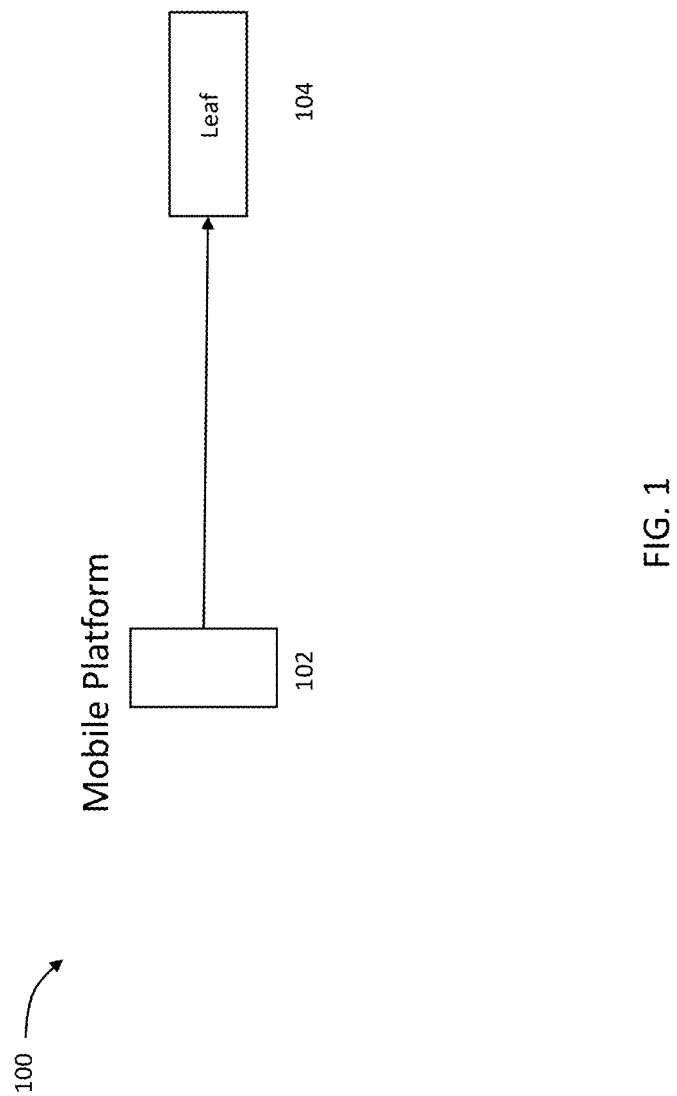
FIG. 1 is a block diagram of a mobile imaging system, according to the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel mobile imaging system is disclosed herein that can provide consistent phenotyping images of a large number of plants and their associated leaves to be used for high precision agriculture and phenotyping studies such that leaves of plants are processed consistently. Towards this end, a new autonomous imaging system is disclosed herein for in vivo plant phenotyping. The system's main innovation is rooted in its vacuum-based leaf-acquisition subsystem which 1) according to one embodiment is configured to bring a single leaf of a plant for imaging; or 2) according to another embodiment is configured to bring a plurality of leaves of one or more plants for faster processing.

The mobile imaging system, according to one of the enumerated embodiments discussed above images a leaf by placing the leaf against a grate in front of a hyperspectral camera or a multispectral camera or both after a mobile platform places the leaf imaging system over a plant. In the case of a hyperspectral image obtained from a hyperspectral camera, a scanning approach is used to scan the imaging area line-by-line. However, in the case of a multispectral image, the multispectral camera is stationary. It should be appreciated that while not an efficient use of a hyperspectral camera, a hyperspectral camera can be used to obtain both a hyperspectral image and one or more multispectral images. Therefore, for various applications, it may be possible to use only one hyperspectral camera for both imaging modalities. The scanning approach is disclosed in the U.S. Provisional Patent Application Ser. No. 63/423,773, to which the present disclosure claims priority. Specifically, according to one embodiment, a rack and pinion system (not shown) known to a person having ordinary skill in the art is employed as a linear actuator to generate articulation of the hyperspectral camera; however, other systems can be used including a lead screw, a belt drive, or a chain drive, all of which are known to a person having ordinary skill in the art.

A GPS module for locating a plant and a micro-controller for operating vacuum and imaging apparatuses are mounted to the mobile platform. The controller processes the image and uploads the predicted plant health parameters to a remote server together with the geolocation and time stamp data of the images. The remote server monitors plant health over a large area with timelines at farm-level, plot-level, or county level.

Figure 2:
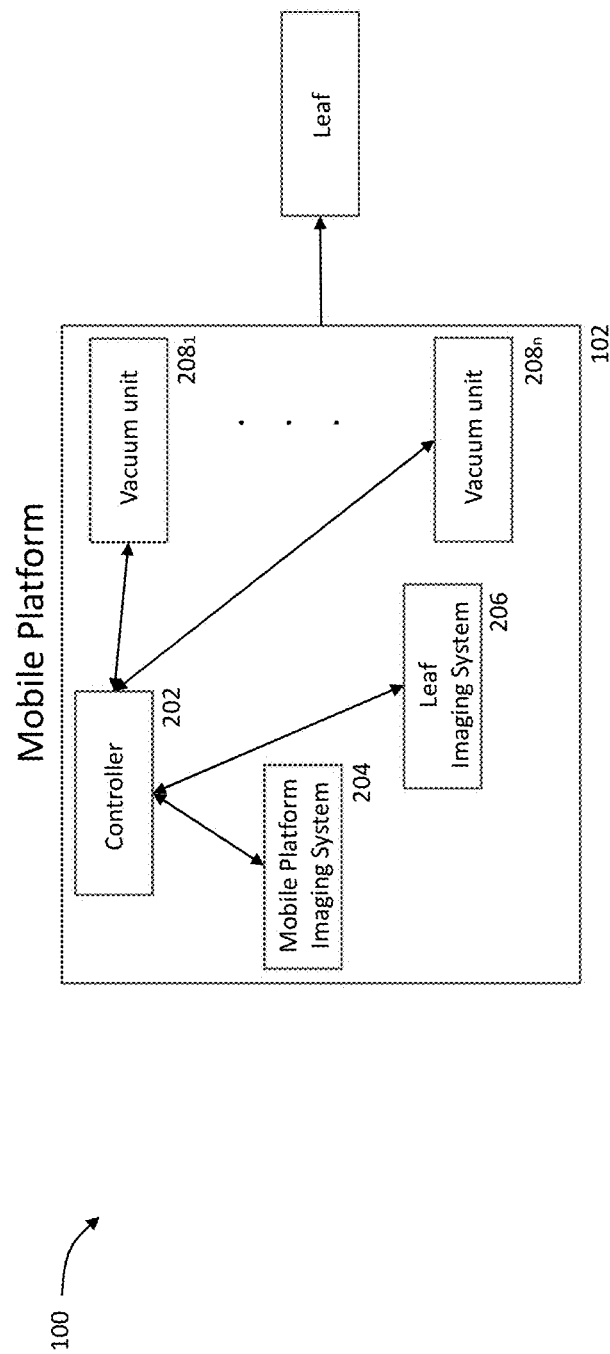
FIG. 2 is a block diagram which provides a more detailed view of the imaging system shown in FIG. 1.

Referring to FIG. 1, a block diagram of a mobile imaging system 100 is provided. The system 100 includes a mobile platform 102 configured to move about plants and provide images of leaves 104 of the plants in an autonomous manner. A more detailed view of the imaging system 100 is shown in FIG. 2. The system 100 shown in FIG. 2 includes a controller 202 configured to control movement of the mobile platform 102 as well as operating other subsystems including i) a mobile platform imaging system 204 in communication with the controller 202 and controlled thereby and configured to provide stereovision images of plants to the controller 202 to thereby allow the controller 202 to control movement of the mobile platform 102, ii) a leaf imaging system 206 configured to obtain images including hyperspectral and multi-spectral images and communicating those images back to the controller 202, and iii) one or more vacuum units 208 (shown as 1, . . . , n) each equipped with one or more fans coupled to a grate, where the grate establishes an air intake to the one or more fans and thus configured to apply vacuum to a leaf of a targeted plant so that the leaf is elevated to the grate in a consistent manner. The controller 202 includes processors configured to execute software housed in a non-volatile memory to operate said subsystems.

For the first embodiment where individual leaves of a plant are imaged, a machine vision module using an INTEL REALSENSE D435 camera (machine vision camera) is used to detect target leaflets and estimate their poses. The machine vision camera is controlled by ROS messages, known by a person having ordinary skill in the art, with known drivers, for convenience in data communication. For each image acquisition, the machine vision camera captures a top view of a plant, e.g., a soybean plant, with an RGB image and a depth map. The returned data are processed to detect the pose (x, y, z, roll, pitch, yaw) of the terminal leaflet (mid leaflet) within the top mature trifoliate which is considered the most representative leaf in soybean phenotyping.

Figure 3:
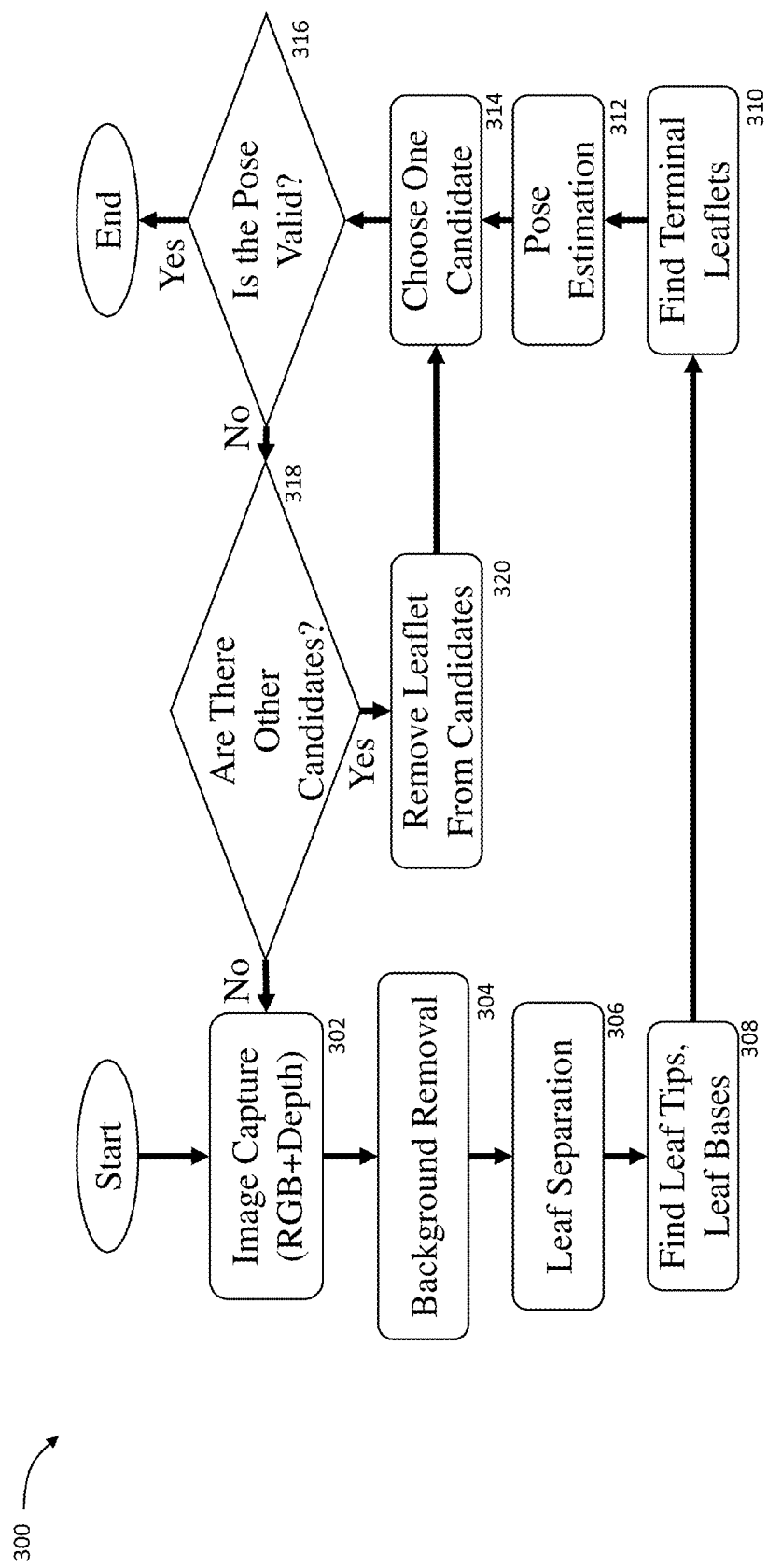
FIG. 3 is a flowchart of an algorithm that forms the basis for a machine vision module, according to the present disclosure.

Referring to FIG. 3, a flowchart 300 is presented that forms the basis for the machine vision module. First an RGB image with depth information is captured as provided in 302. A background removal submodule 304 is then utilized using the depth information provided from the machine vision camera. Since the plant's upper leaves are closer to the machine vision camera in the top view than the soils and the floor, the backgrounds (soils, lower leaves, stems, etc.) in each RGB image (shown in FIG. 4*a* which is a photograph of a plant with the background to be removed) are removed by a mask created from thresholding the corresponding depth map (shown in FIG. 4*b* which is a mask used to remove the background information presented in FIG. 4*a*). The developed machine vision uses 3D information from the machine vision camera to filter out the background, gradients of the 3D information to segment each leaflet, and the ratio between each leaflet's height and area to determine the top matured leaflets. The endpoints are also determined for each leaflet by calculating the furthest two points. To determine which one of the two endpoints is the leaf tip, the positional relationship between the endpoints are compared. However, the results of this background removal contain noise from different sources, because of the mismatched pixels between the RGB image and the depth map. Thus, a greenness indicator was calculated for each pixel using equation (1) for a more refined result.

$$G = g^2/rb \qquad (1)$$

where G is the calculated greenness value; and
r, g, and b are the values of the 3 channels in an RGB image.

Figure 4A:
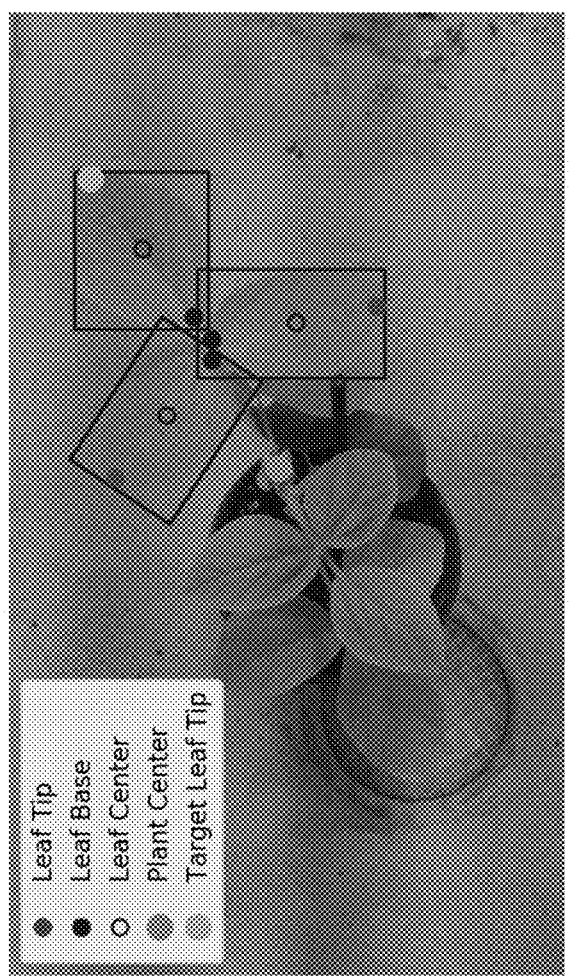
FIG. 4a is a photograph of a plant including background information such as soils, lower leaves, stems, and other information which the background information are to be removed.
Figure 4C:
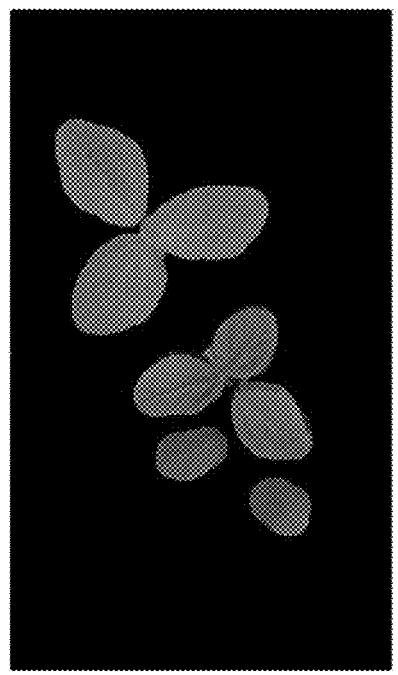
FIG. 4c is an image after the background shown in FIG. 4a has been removed using depth map and greenness indicator.
Figure 4B:
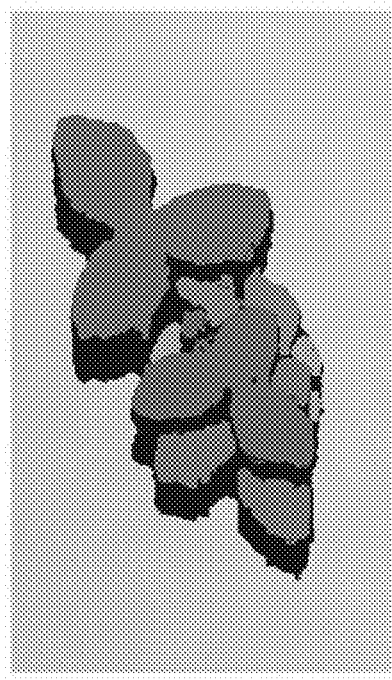
Figure 4D:
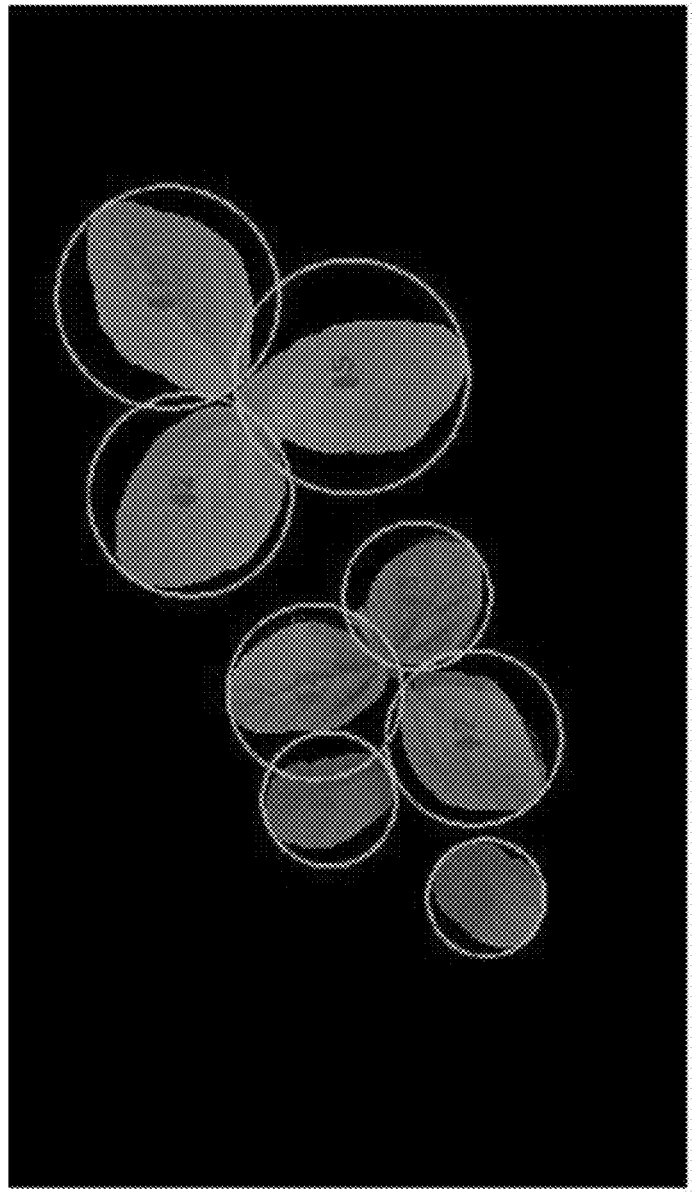
FIG. 4d is an image representing the result from the algorithm of FIG. 3 with leaflets separated with circles and numbered.

FIG. 4c is an image after background shown in FIG. 4a has been removed using depth map and greenness indicator, while FIG. 4d provides the result from the algorithm with leaflets separated (circles) and numbered (numbers).

The image shown in FIG. 4a was then processed by thresholding the depth maps and was segmented using the calculated greenness map. The segmented result (see FIG. 4c) contained mostly leaflets, but the leaflets were not properly separated because of connected stems or overlaps. Thus, the algorithm 300 uses Euclidean Distance Transform to obtain individual leaflets as shown in FIG. 4d, and provided as the leaf separation submodule 306 and find leaf tops and leaf bases submodule 308 in the algorithm 300. Each separated leaflet with its leaf top and leaf bas information is compared using its relative position with others to detect the a target terminal leaflet as provided by submodule 310 in algorithm 300. The orientation of each leaflet is determined by a vector from its base to its tip. While not shown in algorithm, the orientation (i.e., pose) of a finally chosen leaflet can be used to provide micro-adjustment for the mobile imaging system 102 to micro-adjust position of the mobile imaging system 102, according to the present disclosure.

The pose of the target terminal leaflet is next estimated using the pixel coordinates of the tip and base of the leaflet, as provided in the pose estimation submodule 312. With their pixel coordinates known, the depth map, and the machine vision camera's projection matrix, the relative position $(x_r, y_r, Z_r)$ between the vertices and the robotic manipulator are calculated using equation (2), which is a standard transformation from the pixel coordinates to the physical coordinates, as it is known to a person having ordinary skill in the art.

$$\begin{bmatrix} du \\ dv \\ d \end{bmatrix} = KT \begin{bmatrix} x_r \\ y_r \\ z_r \\ 1 \end{bmatrix} = \begin{bmatrix} f_x & 0 & c_x \\ 0 & f_y & c_y \\ 0 & 0 & 1 \end{bmatrix} \begin{bmatrix} a_1 & a_{12} & a_{13} & t_1 \\ a_{21} & a_{22} & a_{23} & t_2 \\ a_{31} & a_{32} & a_{33} & t_3 \end{bmatrix} \begin{bmatrix} x_r \\ y_r \\ z_r \\ 1 \end{bmatrix} \qquad (2)$$

where u and v are the pixel coordinates;
matrix K is the machine vision camera's projection matrix;
matrix T is the transformation matrix from the manipulator coordinate frame to the machine vision camera coordinate frame;
$x_r$, $y_r$, and $Z_r$ are coordinates in the manipulator coordinate frame; and
d is the depth value at pixel (u, v).

The orientation of the leaflet is estimated using the relative position between its two vertices. The pitch angle is calculated by equation (3), and the yaw angle is calculated by equation (4). The roll angle is assumed to be zero.

$$\theta_{pitch} = \sin^{-1}\left(\frac{Z_{tip} - Z_{base}}{\|P_{tip} - P_{base}\|_2}\right) \qquad (3)$$

$$\theta_{yaw} = \mathrm{atan2}\left(\frac{Y_{tip} - Y_{base}}{X_{tip} - X_{base}}\right) \qquad (4)$$

where $P_{tip}$ and $P_{base}$ are the coordinates of the leaflet tip and base in the world coordinate frame; and
X, Y, and Z are the x, y, and z components of the corresponding coordinates.

With the pose of several leaves estimated, one leaf is chosen from a plurality of leaves as the chosen candidate, as provided by the submodule 314 in algorithm 300. The estimated pose is validated by checking if its values are within predetermined ranges, as indicated by the query 316. If the chosen candidate meets the predetermined ranges for yaw, pitch, and roll angles, then the chosen candidate is deemed as a leaf to be used for subsequent hyperspectral and multi-spectral imaging. If the chosen candidate does not meet the predetermined ranges for yaw, pitch, and roll angles, the algorithm first determines if there are other candidate leaves as provided in query 318. If there are other candidate leaves, the algorithm removes the prior leaf from a list of candidate leaflets, as provided by submodule 320 and return to the next such candidate leaf in submodule 314 to repeat the process of determining a valid pose. However, if there are no other candidate leaves, the algorithm returns to the image capture submodule 302 and repeats the process described above. Since soybean plants have vibrations due to airflow and self-movement, each execution of the loop described above returns different results. Each pose was estimated, validated, converted, and sent to the controller 202 shown in FIG. 2 for operation in a ROS integrated Python script. The average execution time for the terminal leaflet detection was 2.59 s.

According to the second embodiment wherein multiple leaves from one or more plant are brought up to a large-size grate, e.g., 5 foot by 5 foot, the algorithm shown in FIG. 3 can be significantly simpler. In such an embodiment, the mobile platform 102 is positioned about a location using predetermined GPS coordinates of a plot and of a plurality of plants. Once positioned, the controller 202 shown in FIG. 2 activates the vacuum units $208_i$ to bring the leaves of the one or more plants to the grate of the mobile unit 102 for subsequent hyperspectral and multi-spectral imaging.

Figure 5A:
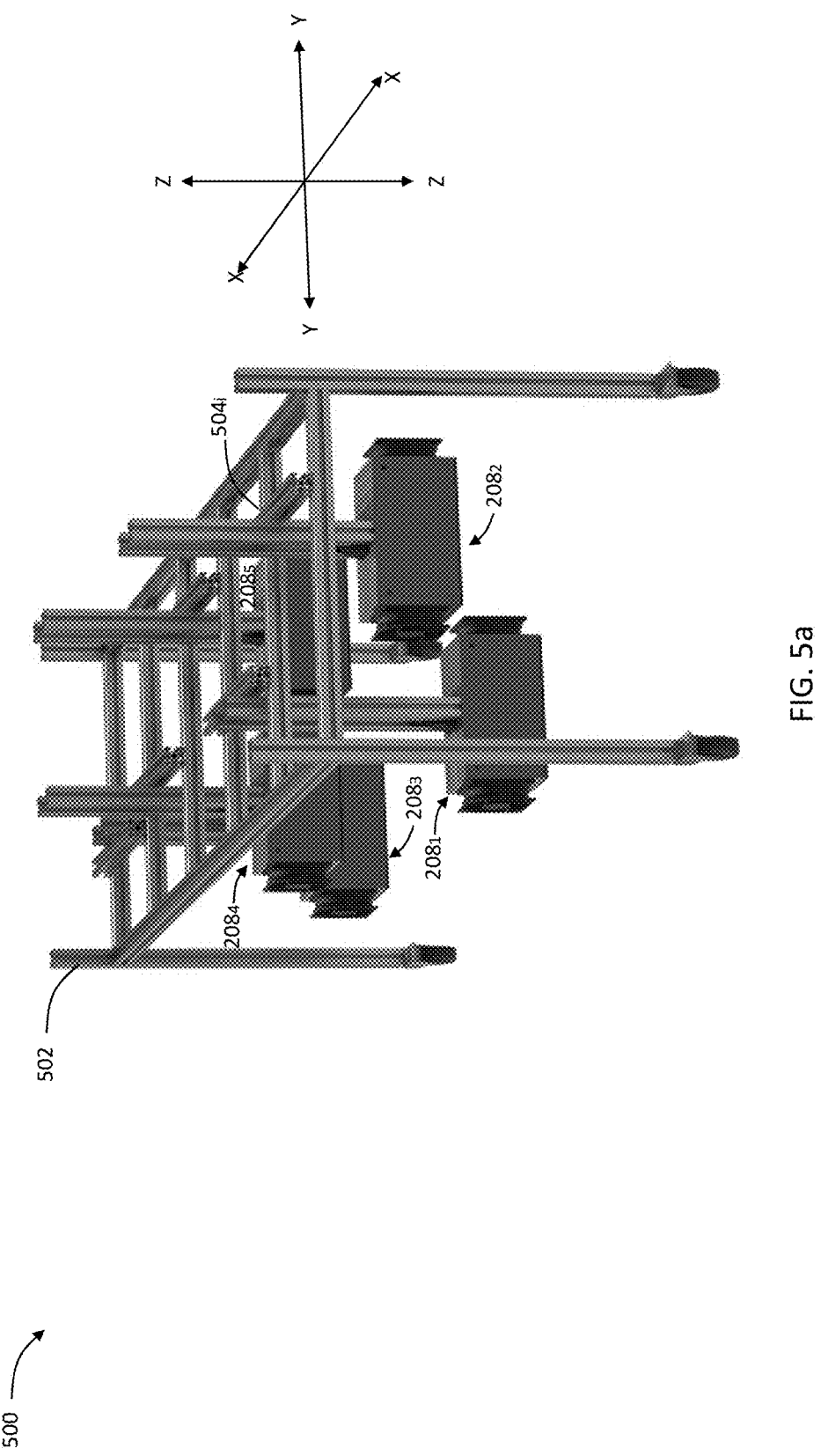
FIGS. 5a and 5b are illustrations of a mobile unit (FIG. 5a), according to a first embodiment, according to the present disclosure, and further depicted in FIG. 5b which is an illustration of two such mobile units of said first embodiment in a field.
Figure 5B:
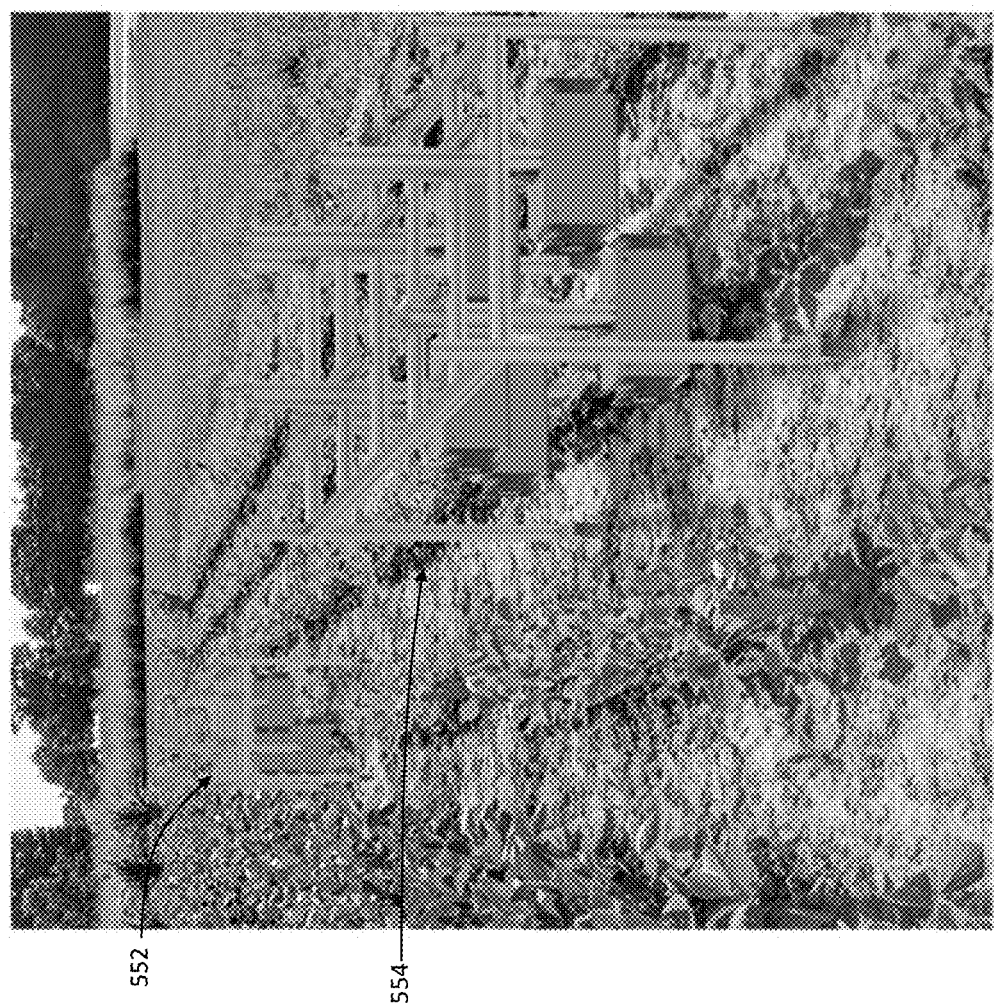

An example of a mobile platform 500, according to the first embodiment, is shown in FIG. 5a which is an illustration of a mobile unit 500, and further depicted in FIG. 5b which is an illustration of two such mobile units 500 in a field. The mobile platform 500, in this embodiment, is a ground-based vehicle providing X-Y adjustments for the one or more vacuum units $208_i$ shown in FIG. 2 (five such vacuum units $208_i$ are shown in FIG. 5a) by sliding the vacuum units $208_i$ along an X-Y coordinate system as shown in FIG. 5a by sliders $504_i$ about a frame 502. Once one or more of the vacuum units $208_i$ is properly positioned along the XY plane based on the steps outlined in algorithm 3 provided in FIG. 3, the vacuum unit $208_i$ is lowered along the Z-axis to the vicinity of a leaflet (see FIG. 4d). At this point the one or more fans in the associated vacuum unit is activated causing a suction against the leaflet and thus causing the leaflet to be elevated to the grate at the bottom of each of the one or more vacuum units $208_i$. The controller 202 discussed in FIG. 2 provides control of the mobile platform to not only provide macro-positioning of the mobile platform 500, 580, or $800_i$, by using a GPS subsystem mounted in the mobile platform but also a beacon positioned within the field as discussed below with respect to FIG. 10, the mobile platform may also use a stereovision camera which may me be one and the same as the machine vision camera to finetune the position of the ground-based vehicle precisely above the plant for the aforementioned leaf pose determination, as discussed above. It should be noted that while there are five vacuum units $208_i$ are shown in FIG. 5a coupled to the mobile platform 500, more or less number of vacuum units can be implemented on each such mobile platform 500 based on specific application. The two mobile platforms 552 and 554, an example of which is shown in FIG. 5a, are shown in FIG. 5b in a field as each traverses the field to provide images from the plants.

Figure 5C:
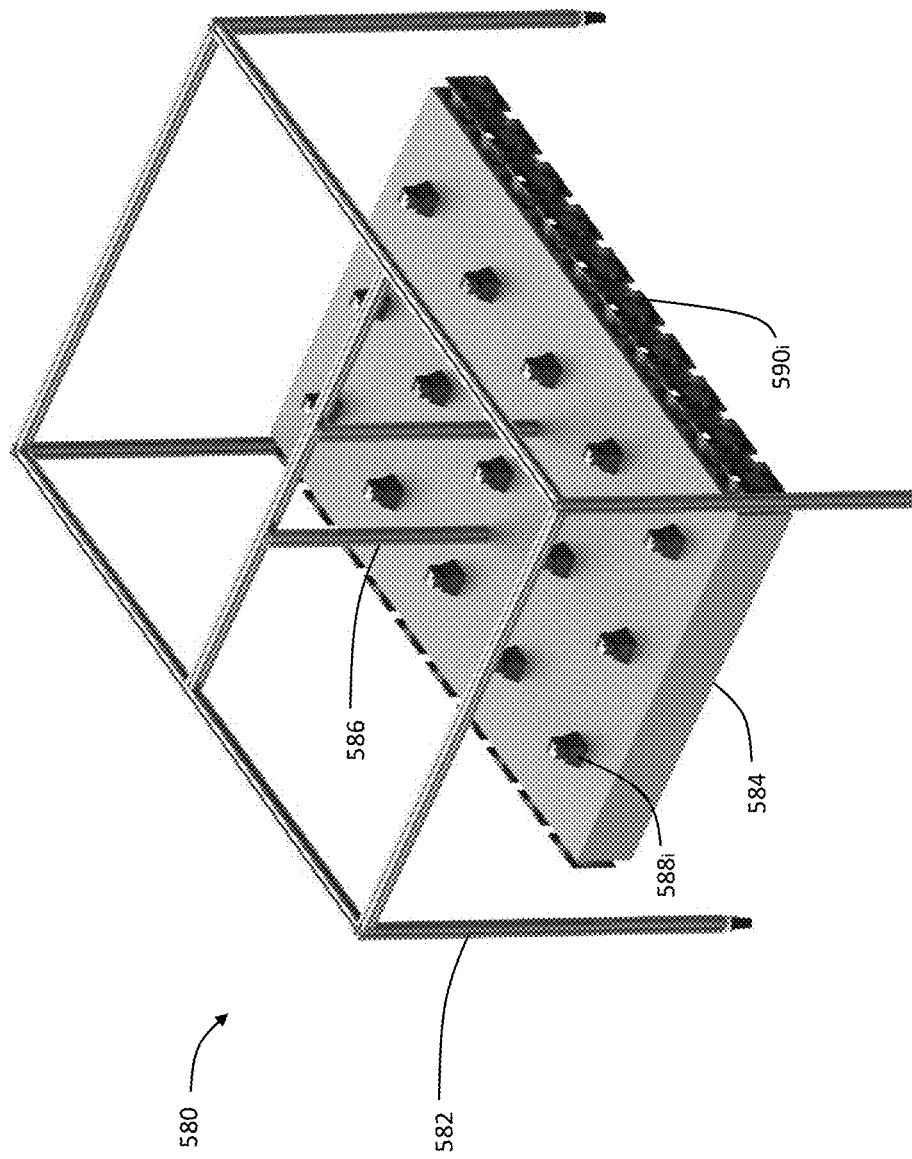
FIG. 5c is an illustrations of a mobile unit, according to a second embodiment, according to the present disclosure.

Referring to FIG. 5c, a schematic of an example of a mobile platform 580, according to the second embodiment, is shown. The mobile platform 580 includes a frame 582 to which a large vacuum unit 584 is coupled. The vacuum unit 584 allows for a large grate (not shown) thus allowing for multiple leaves to be elevated to the grate for simultaneous hyperspectral or multispectral imaging. The mobile platform 580 also includes a vertical elevators 586 configured to lower the vacuum unit 584 on to the vicinity of leaves of one or more plants. Also shown are imaging systems $588_i$ which include both RGB and depth camera(s), the stereovision camera as well as a hyperspectral camera, a multispectral camera, or both a hyperspectral and multispectral cameras distributed about the vacuum unit 584 for obtaining RGB and depth images as well as hyperspectral and multispectral images. As discussed above, a hyperspectral camera operates based on line scanning. Thus, if imaging systems $588_i$ include hyperspectral cameras, then each of those cameras requires a linear actuator discussed above and further disclosed in the U.S. Provisional Patent Application Ser. No. 63/423,773, to which the present disclosure claims priority. The line scanning may be based on zones, each associated with the a zone defined by the corresponding imaging systems $588_i$. Also shown are a series of fans distributed along sides of the vacuum unit to provide a robust vacuum for elevating a plurality of leaves at the same time. The mobile platform 580 is a ground-based unit with wheels and propulsion (not shown) to allow the mobile platform 580 to move from a first position to a second position based on onboard GPS (not shown) and beacons disposed on the field.

Figure 6:
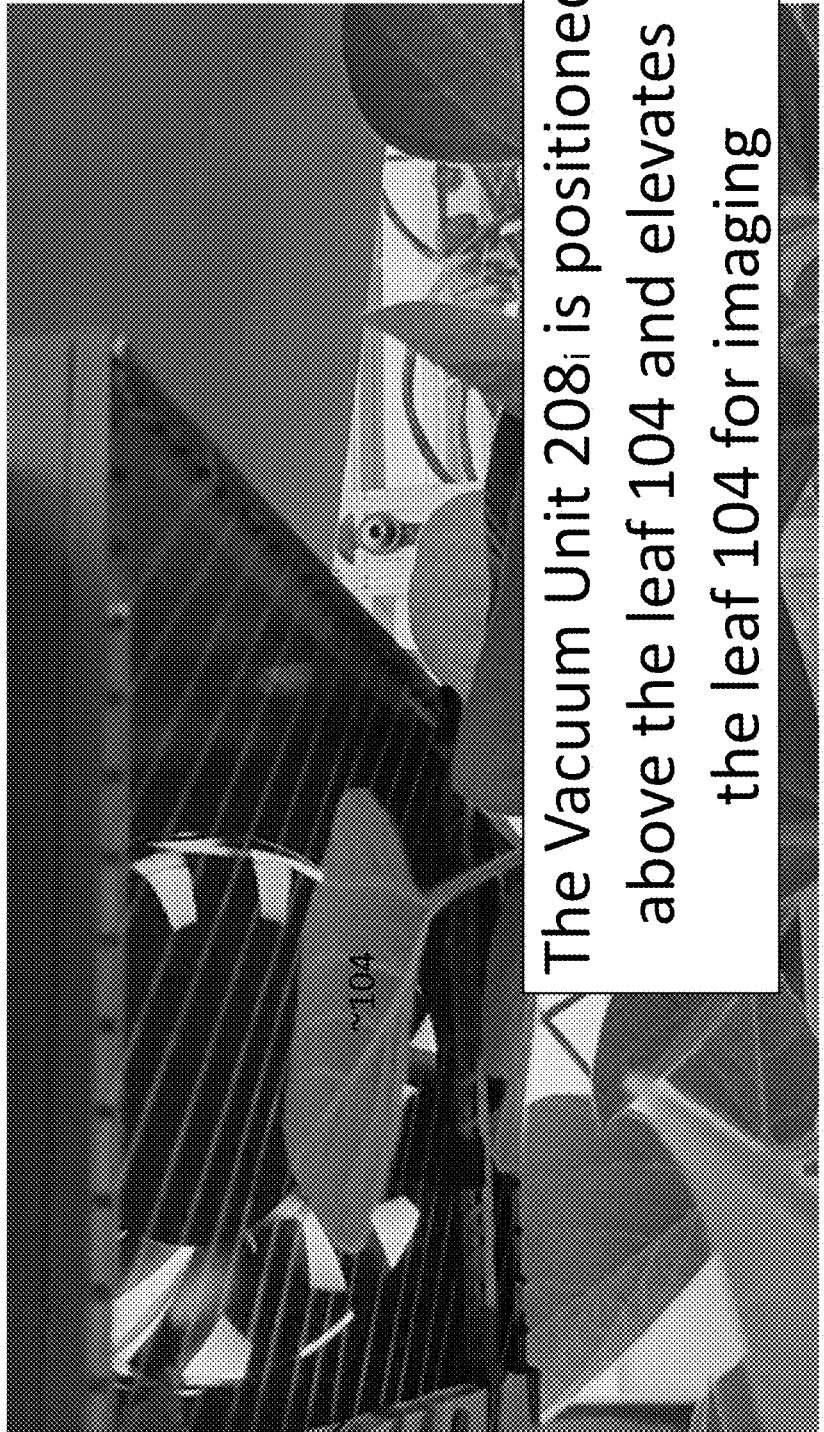
FIG. 6 is an illustration of a grate disposed at the base of a vacuum unit, which further represents the vacuum unit in operation by properly adjusting the position of the vacuum unit above the leaflet and providing suction to the leaflet to thereby elevating the leaflet to the grate.
Figure 7:
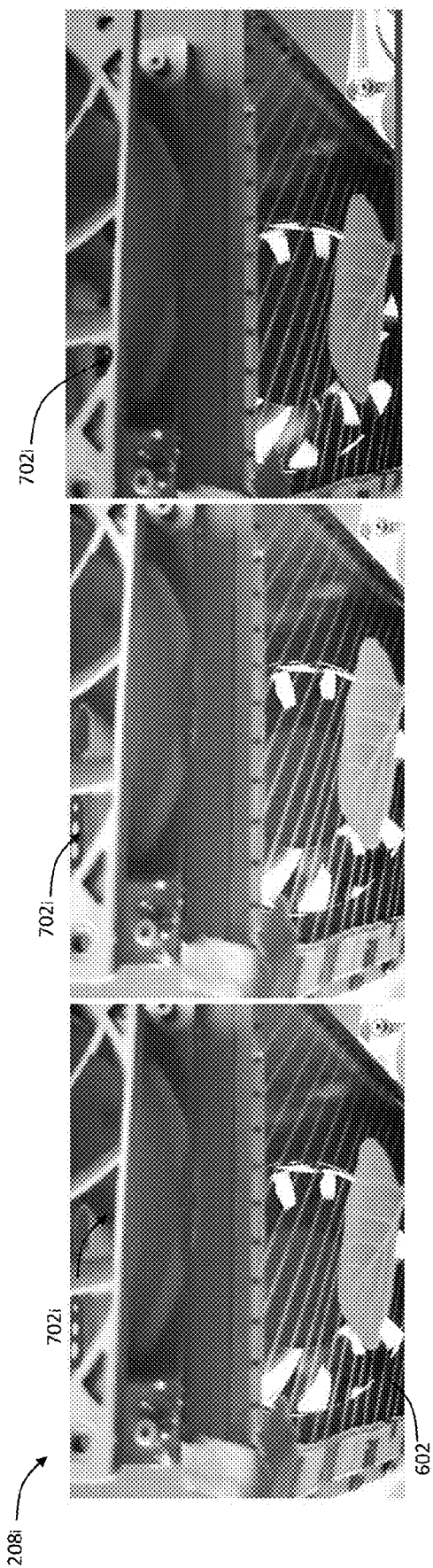
FIG. 7 provides several images within the vacuum units with various color light emitting diodes (LEDs) configured to illuminate the leaflet that is against the grate and in cooperation with a multispectral camera configured to obtain hyperspectral and/or a multispectral images, a multispectral camera configured to provide multispectral images, or both a hyperspectral camera and a multispectral camera.

FIG. 6 which is an illustration of a grate disposed at the base of a vacuum unit 2081, represents the vacuum unit $208_i$ in operation by properly adjusting the position of the vacuum unit $208_i$ above the leaflet 104 and providing suction to the leaflet 104 to thereby elevating the leaflet to the grate 602. Referring to FIG. 7, within the vacuum units $208_i$ are various color light emitting diodes (LEDs) $702_i$ configured to illuminate the leaflet 104 that is against the grate 602 and in cooperation with a hyperspectral camera, a multispectral camera, or both configured to obtain hyperspectral and/or multispectral images.

Figure 8:
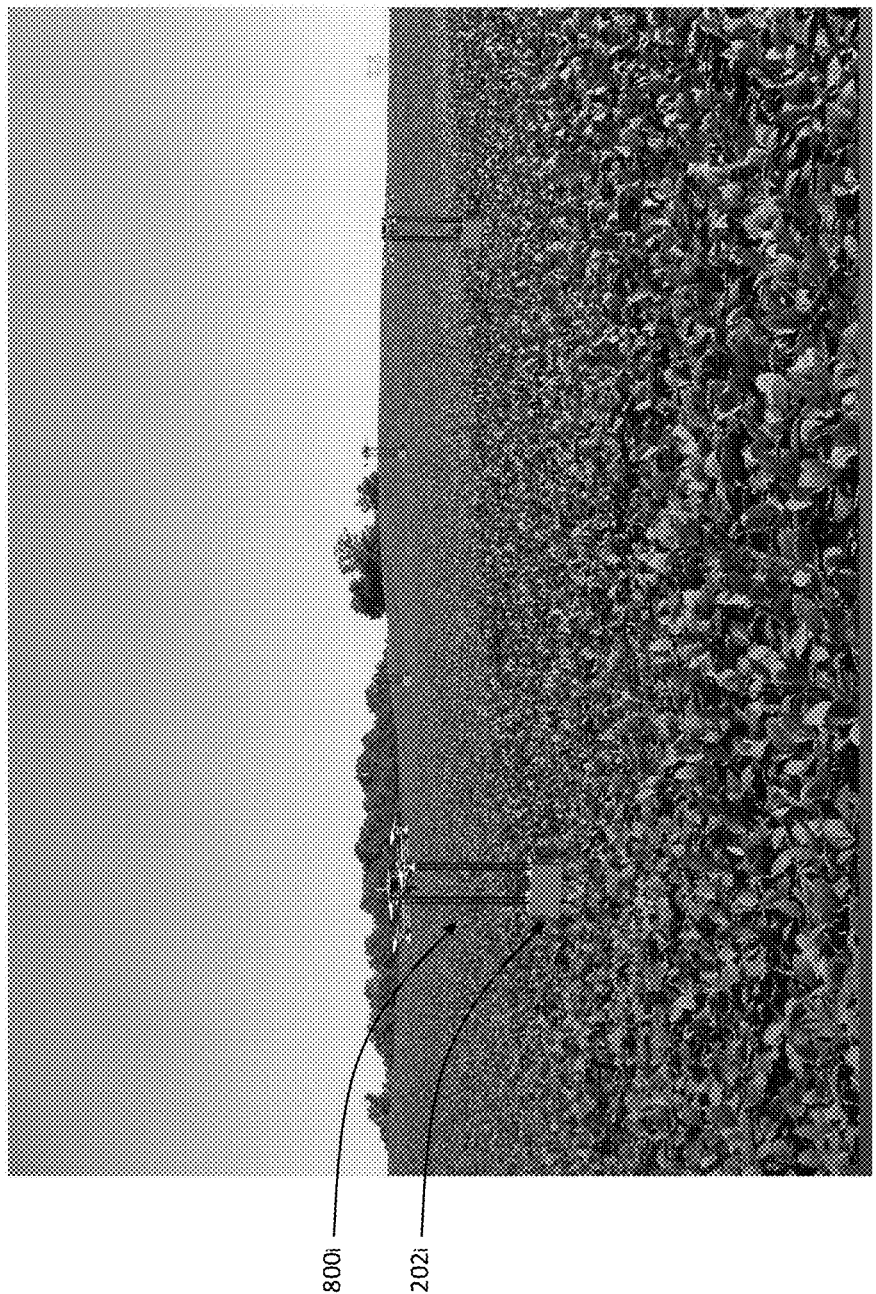
FIG. 8 is an image of a plurality of another mobile platforms (an aerial vehicle) depicted in a field, each equipped with a corresponding vacuum unit.

Referring to FIG. 8, a plurality of another mobile platform $800_i$ (an aerial vehicle) is also depicted in a field each equipped with a corresponding vacuum unit 2081. As shown in FIG. 8, there are no X-Y-Z micro-adjustments based on moving the vacuum unit $208_i$ along an X-Y-Z axis as shown in FIG. 5a. Here the controller 202 discussed in FIG. 2 provides control of the aerial vehicle to not only provide macro-positioning of the mobile platform $800_i$, e.g., by using a GPS subsystem mounted in the mobile platform $800_i$, but also a beacon positioned within the field, as discussed with respect to FIG. 10; the mobile platform also uses a stereovision camera to finetune the position of the aerial vehicle precisely above the plant for the aforementioned leaf pose determination.

Figure 9:
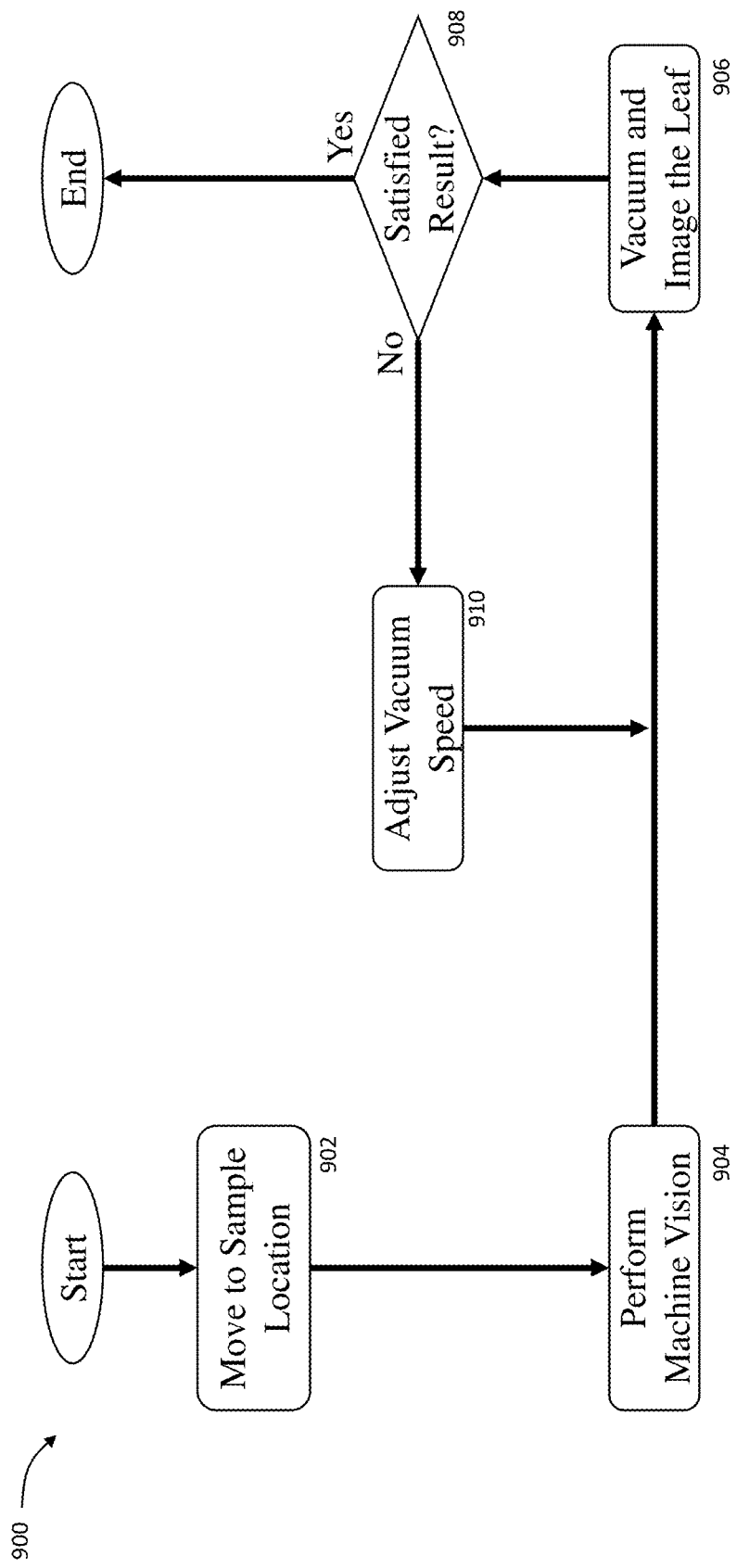
FIG. 9 is a flowchart that is used by a controller shown in FIG. 2 that can control the operations of a ground-based mobile platform shown in FIGS. 5*a* and 5*c* or an aerial mobile platform shown in FIG. 8.

Referring to FIG. 9, a flowchart 900 is provided that is used by the controller 202 of FIG. 2 that can control the operations of the mobile platform 500 (FIG. 5a) or $800_i$ (FIG. 8), i.e., ground-based or aerial. Specifically, the controller 202 (FIG. 2) controls the mobile platform 500 (FIG. 5a) or $800_i$ (FIG. 8) so it first approaches a sample location, e.g., where a plant is located whose leaves are to be imaged, as indicated by block 902. As discussed above, the movement of the mobile platform 500 (FIG. 5a) or $800_i$ (FIG. 8) is via a GPS subsystem provided within the mobile platform and its position may be further defined by a beacon provided in the field as discussed with respect to FIG. 10. Once the mobile platform 500 (FIG. 5a) or $800_i$ (FIG. 8) has moved to the sample location, the mobile platform is positioned over the plant and then it begins to perform machine vision as discussed above to identify the leaflet and its boundaries, as provided by block 904. The controller then uses the output of the machine vision steps of which are outlined by algorithm 300 in FIG. 3 to provide micro-adjustments to the position of the vacuum unit(s) $208_i$ (see FIG. 5a). For example, for the ground-based mobile platform 500 (FIG. 5a) the final micro-adjustments are made by sliding the vacuum unit(s) $208_i$ along the X-Y-Z axes; but for the aerial mobile platform $800_i$, the aerial vehicle $800_i$ makes appropriate aerial positioning adjustments so that the vacuum unit is properly positioned above the leaflet. At this point the controller 202 (FIG. 2) activates the vacuum unit(s) $208_i$ followed by obtaining images from the leaflet, as provided by block 906. According to one embodiment, the controller 202 (FIG. 2) is configured to transmit the obtained image to a central database, e.g., shown as RTK base station in FIG. 10 or other base stations, in which it is determined via machine learning or other approaches whether the obtained image is acceptable, as shown by the query 908. If acceptable, then the algorithm 900 is done. If not acceptable, the controller 202 (FIG. 2) adjust speed of fans in the vacuum unit $208_i$ as shown in block 910 and repeats the process back to block 906.

Figure 10:
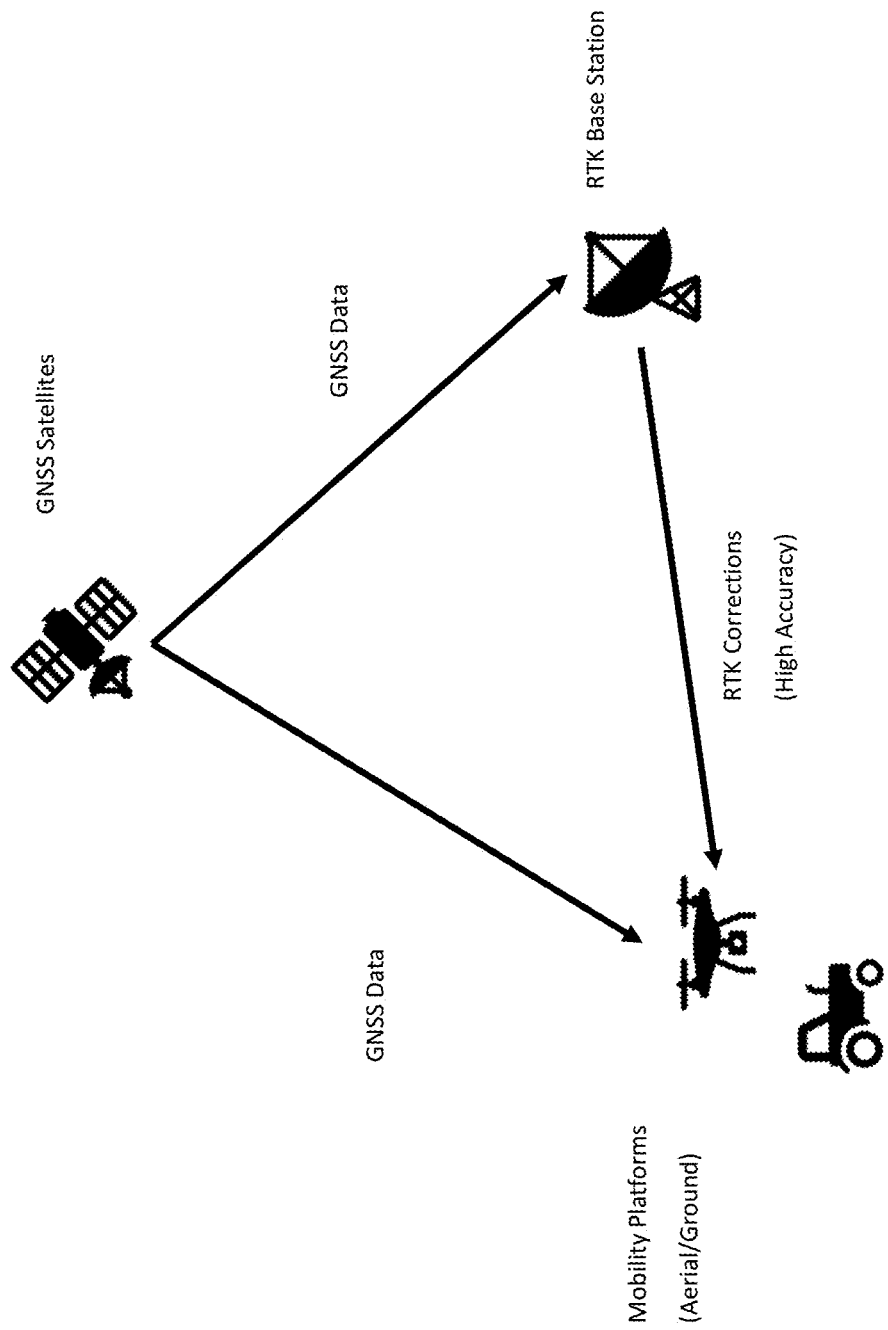
FIG. 10 is schematic of how a controller shown in FIG. 2 provides control of a mobile platform shown in FIGS. 5*a*, 5*c*, and 8 to not only provide macro-positioning of the mobile platform by using a GPS subsystem mounted in the mobile platform but also a beacon positioned within the field.

Referring to FIG. 10, a schematic of real-time kinematics (RTK) is provided which is the application of surveying to correct for common errors in Global Positioning System (GPS). A GPS-based system typically includes a receiver unit and uses the Global Navigation Satellites System (GNSS) to locate a position worldwide in real-time, with an accuracy of 2 m. RTK has two units, a base station and a receiver. A base station is fixed at a position whose precise location is measured through other independent methods; thus, absolute position of the base station is known with a high degree of accuracy. The base station receives GNSS data and compares the received readings with its location to calculate an error associated with the GNSS in real-time. It sends the compared results, also known as corrections, to the receiver, usually by a radio frequency signal. In operation, a mobility platform, according to the present disclosure equipped with RTK receivers receive both GNSS readings from the GNSS and corrections from the base station. The corrections compensate for the error in GNSS readings to achieve centimeter-level positioning accuracy as shown in FIG. 10.

It should be noted that software provided in memory and operated by a processor is within the skillset of a person having ordinary skill in the art based on the disclosed block diagrams and flowcharts.

Those having ordinary skill in the art will recognize that numerous modifications can be made to the specific implementations described above. The implementations should not be limited to the particular limitations described. Other implementations may be possible.

The invention claimed is:

1. An autonomous system for providing consistent images of leaves of plants, comprising:
   a mobility unit configured to move from an originating position to a position about a plant in a field;
   one or more automated vacuum units coupled to the mobility unit configured to be positioned above one or more leaves of the plant, the one or more vacuum units each having one or more fans coupled to an air inlet having a grate, and configured to elevate the one or more leaves of the plant onto the grate;
   one or more imaging systems each having one or more cameras configured to obtain images from the one or more leaves of the plant; and
   a controller configured to control position of the mobility unit and activate the one or more imaging system to thereby obtain images from the one or more leaves of the plant.

2. The autonomous system of claim 1, wherein the mobility unit is an aerial system.

3. The autonomous system of claim 2, wherein the aerial system includes a plurality of propellers.

4. The autonomous system of claim 3, wherein the number of propellers is 3.

5. The autonomous system of claim 3, wherein the number of propellers is 4.

6. The autonomous system of claim 1, wherein the mobility unit is a ground-based mobility system.

7. The autonomous system of claim 1, wherein the one or more cameras includes a hyperspectral camera capable of generating hyperspectral images.

8. The autonomous system of claim 1, wherein the one or more cameras includes a multispectral camera capable of generating multispectral images.

9. The autonomous system of claim 8, the one or more imaging systems each disposed within a corresponding one or more vacuum units and each further comprising a plurality of light emitting diodes projecting light at different wavelengths onto the leaf.

10. The autonomous system of claim 1, wherein each of the one or more imaging systems further includes an RGB and depth camera capable of providing images including color and depth information related to the leaf of the plant, wherein the information from the RGB and depth camera is used by the controller to locate a leaf from the one or more leaves according to a predefined pose.

11. The autonomous system of claim 1, wherein each of the one or more imaging systems further includes a stereovision camera configured to provide a stereo image, wherein the controller receives the stereo images.

12. The autonomous system of claim 1, the controller configured to carry out machine vision by performing steps:
    a) capture images of a plant;
    b) remove background from the captured images;
    c) identify and separate the leaf in the background-removed images;
    d) identify and positionally locate a tip of the leaf from the leaf-separated image;
    e) identify and locate a terminal leaflet of the leaf;
    f) estimate pose of the leaf; and
    g) finetune position of the mobile unit in accordance with the estimated pose of the leaf.

13. The autonomous system of claim 12, wherein the system controller dynamically determines whether the estimated pose of the leaf is within a predetermined threshold as the mobility unit moves the one or more imaging systems towards the leaf.

14. A method of autonomously providing consistent images of leaves of plants, comprising:
    moving a mobility unit from an originating position to a position about a plant in a field;
    positioning one or more automated vacuum units coupled to the mobility unit above one or more leaves of the plant, the one or more vacuum units each having one or more fans coupled to an air inlet having a grate, and configured to elevate the one or more leaves of the plant onto the grate;
    obtaining images from the one or more leaves of the plant by one or more imaging systems each having one or more cameras; and
    controlling position of the mobility unit by a controller and activate the one or more imaging system to thereby obtain images from the one or more leaves of the plant.

15. The method of claim 14, wherein the mobility unit is an aerial system.

16. The method of claim 14, wherein the mobility unit is a ground-based mobility system.

17. The method of claim 14, wherein the one or more cameras includes a hyperspectral camera capable of generating hyperspectral images.

18. The method of claim 14, wherein the one or more cameras includes a multispectral camera capable of generating multispectral images.

19. The method of claim 14, the one or more imaging systems are each disposed within a corresponding one or more vacuum units and each further comprising a plurality of light emitting diodes projecting light at different wavelengths onto the leaf.

20. The method of claim 14, wherein each of the one or more imaging systems further includes an RGB and depth camera capable of providing color and depth information related to the leaf of the plant, wherein the information from the RGB and depth camera is used by the controller to locate a leaf from the one or more leaves according to a predefined pose.

21. The method of claim 20, wherein each of the one or more imaging systems further includes a stereovision camera configured to provide stereovision images, and wherein the controller receives the stereovision images.

22. The method of claim 14, the controller configured to carry out machine vision by performing steps:
    h) capture images of a plant;
    i) remove background from the captured images;
    j) identify and separate the leaf in the background-removed images;
    k) identify and positionally locate a tip of the leaf from the leaf-separated image;
    l) Identify and locate a terminal leaflet of the leaf;
    m) estimate pose of the leaf; and
    n) finetune position of the mobile unit in accordance with the estimated pose of the leaf.

23. The method of claim 22, wherein the system controller dynamically determines whether the estimated pose of the leaf is within a predetermined threshold as the mobility unit moves the one or more imaging systems towards the leaf.

* * * * *